United States Patent [19]

Ramachandran et al.

[11] Patent Number: 5,179,215

[45] Date of Patent: Jan. 12, 1993

[54] PROCESS FOR THE PRODUCTION OF PETROCHEMICALS

[75] Inventors: Ramakrishnan Ramachandran, Allendale; Donald L. MacLean, Annandale, both of N.J.

[73] Assignee: The BOC Group, Inc., New Providence, N.J.

[21] Appl. No.: 661,794

[22] Filed: Feb. 27, 1991

[51] Int. Cl.$^5$ ............... C07D 307/36; C07D 307/89; C07D 307/34; C07C 253/00

[52] U.S. Cl. ............... 549/262; 549/247; 549/248; 549/249; 549/250; 549/256; 549/257; 549/258; 549/259; 549/260; 549/261; 558/318; 558/320; 558/327; 558/330; 562/545; 568/476; 568/513; 568/910; 570/224; 570/243; 570/248; 570/251

[58] Field of Search ............... 549/259, 247–250, 549/256–262, 518; 570/248, 251, 224, 243; 558/318, 320, 327, 330; 568/910, 476, 513; 562/545

[56] References Cited

U.S. PATENT DOCUMENTS

| | | | |
|---|---|---|---|
| 3,904,652 | 9/1975 | Frank | 549/259 |
| 3,904,653 | 9/1975 | Milberger | 549/256 |
| 4,118,403 | 10/1978 | White | 549/262 |
| 4,238,460 | 12/1980 | Aiken et al. | 549/262 |
| 4,263,211 | 4/1981 | Keunecke et al. | 549/262 |
| 4,282,013 | 8/1981 | Franklin et al. | 549/262 |
| 4,352,755 | 10/1982 | Higgins et al. | 549/258 |
| 4,391,880 | 7/1983 | Tsao | 549/262 |
| 4,435,581 | 3/1984 | Miserlis | 549/257 |
| 4,530,826 | 7/1985 | Ohashi et al. | 549/257 |
| 4,658,042 | 4/1987 | Watanabe et al. | 549/262 |
| 4,675,420 | 6/1987 | Block et al. | 549/259 |
| 4,748,140 | 5/1988 | Blum et al. | 549/258 |
| 4,987,239 | 1/1991 | Ramachandran | 549/262 |
| 5,045,297 | 9/1991 | Bonifaz et al. | 423/247 |

Primary Examiner—Cecilia Tsang
Attorney, Agent, or Firm—Coleman R. Reap; Larry Cassett

[57] ABSTRACT

An improved process is provided for the production of a petrochemical by the vapor phase reaction of a hydrocarbon with an oxygen-containing gas in the presence of a suitable catalyst to produce a flammable gaseous product stream comprising the desired petrochemical, unreacted hydrocarbon, oxygen, carbon monoxide and carbon dioxide. In the improved process, a cooled or liquefied inert gas is injected as a quench fluid into the gaseous product stream exiting the hydrocarbon oxidation reactor, thereby cooling the stream to a temperature below the autoignition temperature of the flammable components of the stream, the petrochemical is recovered from the gaseous product and unreacted hydrocarbon is removed from the gaseous product and recycled to the reactor.

40 Claims, 1 Drawing Sheet

PROCESS FOR THE PRODUCTION OF PETROCHEMICALS

FIELD OF THE INVENTION

The present invention is directed to a process for producing a petrochemical from a hydrocarbon and an oxygen-containing gas in the presence of a suitable catalyst, and more particularly to a process for reducing or eliminating the hazard of an explosion or fire in a vapor phase reactor system in which a petrochemical is produced from a hydrocarbon and oxygen.

BACKGROUND OF THE INVENTION

Many petrochemical products are produced by the oxidation of an appropriate hydrocarbon in the vapor phase over a suitable catalyst. For example, maleic anhydride is produced commercially by the vapor phase oxidation of benzene or straight-chain $C_4$ hydrocarbons (hydrocarbons containing four carbon atoms), such as n-butane, butene or butadiene, with oxygen over a vanadium-phosphorus oxide catalyst. Similarly, unsaturated nitriles are produced by the ammoxidation of a saturated or olefinically unsaturated hydrocarbon with oxygen in the presence of ammonia and an appropriate catalyst; alkylene oxides are produced by the oxidation of lower alkanes or alkenes with oxygen in the presence of an appropriate catalyst; and unsaturated chlorinated hydrocarbons are produced by the oxidation of lower alkanes or alkenes with oxygen in the presence of an appropriate catalyst. Air is generally used as the source of the oxygen because of its low cost and ready availability. The reaction can be carried out in any suitable reactor, such as a fixed, fluidized or transport bed reactor, and it produces the petrochemical product, and generally carbon monoxide (CO), carbon dioxide ($CO_2$), water, and smaller amounts of other partially oxidized by-products. The reaction equipment train generally consists of a reactor, in which the desired product is produced, a petrochemical recovery unit such as a scrubber, in which the product is recovered from the reactor effluent gases by means of water or other solvent for the desired product, and means for further treating the scrubbed effluent gases.

In the past it was common to practice the above-described processes on a single pass basis with the conversion of hydrocarbon being maximized. This often resulted in a low overall efficiency, since the selectivity to the desired product may have been below the maximum. Consequently, the product-depleted effluent gas contained, in addition to unreacted hydrocarbon, considerable amounts of CO and $CO_2$. These products were usually incinerated, so that the only return realized from them was heat value. In later processes a portion of the product-depleted effluent gas was recycled, the conversion of the hydrocarbon feedstock was lowered and the selectivity of hydrocarbon conversion to desired products was maximized. The remainder of the effluent was purged from the system to prevent the build-up of CO, $CO_2$ and nitrogen (introduced into the system when air is used as the source of oxygen). These improvements resulted in a reduced "per pass" conversion but the overall efficiency of the process was increased.

Federal Republic of Germany (FRG) Patent Application Disclosure 25 44 972 discloses a maleic anhydride manufacturing process in which the reactor feed comprises $C_4$ hydrocarbons, air, CO and $CO_2$. In the process of this patent maleic anhydride is recovered from the reactor effluent gas stream and a portion of the remaining stream is recycled. This patent also teaches recovering butane by temperature swing adsorption from the non-recycled gas stream and recycling the recovered butane to the reactor.

A major problem associated with the gas phase production of a petrochemical by the oxidation of hydrocarbons with oxygen is that since the reaction is carried out at elevated temperatures, there is an ever-present danger of a fire or an explosion in the reactor, or the equipment or pipelines associated with the reactor, as a result of the decomposition of unreacted hydrocarbons. The propensity of the hydrocarbons to decompose is enhanced by the presence of catalyst, and the tendency toward decomposition is particularly enhanced in fluidized bed or transport bed reactors. Accordingly, efforts are constantly made to maintain conditions in the reactor and associated equipment such that the mixture remains outside of the flammability range, or at least out of the autoignition range.

U.S. Pat. No. 3,904,652 teaches a gas phase maleic anhydride manufacturing process in which oxygen is used as the oxidizing gas and an inert gas, such as nitrogen, argon, helium or a lower hydrocarbon is fed into a fixed bed reactor with the n-butane and oxygen, the inert gas serving as a diluent to reduce the concentrations of oxygen and butane in the reactor to below the point at which they form a flammable mixture. In the disclosed process, a portion of the gaseous effluent, which contains, in addition to butane, carbon monoxide, carbon dioxide and the inert gas, is recycled.

U.S. Pat. No 4,352,755 discloses a recycle process for the vapor phase manufacture of maleic anhydride by reacting a straight-chain $C_4$ hydrocarbon with oxygen in the presence of $CO_2$. In the process disclosed in this patent the gaseous mixture may contain up to 30 volume percent of carbon dioxide as the inert diluent and contains at least 25 volume percent $C_4$ hydrocarbon. This patent states that at most 2% v/v and more preferably at most 1% v/v of carbon monoxide is present in the oxidation stage. In the process of this patent, the presence of large amounts of $C_4$ hydrocarbon can render the gas mixture in the system flammable, especially in the region of the reactor outlet.

As is well known, under a given set of conditions, including composition and pressure, the flammability and autoignitability of a gaseous hydrocarbon-oxygen mixture is dependent upon, inter alia, the temperature of the gaseous mixture. At low temperatures, the gaseous mixture may have a relatively small flammability range, but as the temperature of the mixture rises, its flammability range increases. For instance, at low temperatures (lower than about 300° C.) the mixture may not be autoignitable. However, as the temperature rises, a point is eventually reached at which the mixture becomes autoignitable. When this point is reached, the mixture will ignite and burn or explode, which event can result in damage to equipment and serious injury or death to persons in the vicinity of the fire or explosion.

A feed mixture entering the oxidation reactor of a vapor phase petrochemical manufacturing plant may have a composition that, at higher temperatures, would render it self-ignitable. The reaction occurring in the reactor upon contact of the feed mixture with the catalyst often raises the temperature of the mixture to the point at which it would ordinarily ignite, however the mixture usually does not ignite in the reactor, apparently because the catalyst suppresses ignition of the mixture. On the other hand, since very little, if any, catalyst is entrained in the hot product gas stream leaving the reactor, it often happens that the gas stream leaving the reactor is subject to self-ignition. To prevent such an occurrence, the mixture leaving the reactor is conventionally rapidly cooled by heat exchange to a temperature below its autoignition point. It sometimes happens, however, that the reactor exit heat exchanger fails to cool the product gas stream rapidly enough to prevent it from igniting, and a devastating and costly fire occurs.

Because of the considerable danger of injury to personnel and damage to equipment, efforts to find new and improved ways to eliminate or reduce the hazard of fire or explosion in chemical plants are continuously made. The present invention provides a method and apparatus for reducing the likelihood of a fire or explosion in a plant for the vapor phase manufacture of petrochemicals.

SUMMARY OF THE INVENTION

The present invention provides an improvement in a recycle process and apparatus for manufacturing petrochemicals by the vapor phase oxidation of a hydrocarbon with oxygen in the presence of a suitable catalyst. The invention comprises introducing a cooled or liquefied inert gas as a quench fluid into the gaseous product stream exiting the reaction zone of a hydrocarbon oxidation reactor in which the petrochemical is produced to rapidly cool the stream to below its autoignition point.

According to the process of the invention, one or more hydrocarbon precursors, such as o-xylene, naphthalene, benzene or saturated or unsaturated straight-chain hydrocarbons containing four carbon atoms are contacted with an oxygen-containing gas in a suitable oxidation reactor to produce a gaseous product stream containing a petrochemical, e.g. a cyclic anhydride, such as phthalic anhydride or maleic anhydride, the specific petrochemical product produced depending upon which hydrocarbon or hydrocarbons are reacted, the particular catalyst used and, in some cases, the presence of other reactants. The hydrocarbon oxidation reactor product stream also contains carbon monoxide and carbon dioxide, and generally unreacted hydrocarbon(s), oxygen, inert diluents introduced into the reactor, if any, and possibly small amounts of other reaction by-products. As or shortly after the hot gaseous product stream leaves the oxidation reaction zone, a quench fluid comprising cooled or liquefied inert gas is injected into the stream to rapidly cool it to below the autoignition temperatures of its flammable components. The cooled product stream can be further cooled in a heat exchanger, if desired, and it is then introduced into a petrochemical removal means, which, for example, may be a condenser or a scrubber in which it is contacted with a liquid solvent which removes substantially all of the petrochemical product from the gas stream. The petrochemical product is recovered from the product removal means as a liquid. All or a Portion of the petrochemical product-depleted gaseous stream is then treated in a separator which removes substantially all of the injected inert gas, some or all of the carbon dioxide and some or all of the carbon monoxide in the gaseous effluent stream. The remainder of the gaseous effluent, comprised of unreacted hydrocarbon and possibly carbon dioxide and carbon monoxide is recycled to the inlet to the hydrocarbon oxidation reactor.

In one embodiment of the invention, the inert gas quench fluid is provided from an external source. In an alternate embodiment, expended quench fluid is separated from the petrochemical-depleted gas stream and used as the quench stream.

In a preferred embodiment of the process aspect of the invention the oxygen-containing gas is substantially pure oxygen. In another preferred embodiment, the unreacted hydrocarbon and inert gas are removed from the petrochemical-depleted effluent by adsorption, absorption or membrane separation.

Another novel aspect of the invention is the system in which the process of the invention is carried out. According to one embodiment, the system comprises a hydrocarbon reactor, a quenching fluid introduction means, a petrochemical product recovery unit, such as a scrubber or a condenser, an unreacted hydrocarbon and inert gas separator and connecting conduits. According to an alternate embodiment, the system comprises a hydrocarbon reactor, a quenching fluid introduction means, a petrochemical recovery unit, a separator and an inert gas recycle line in which is located a gas cooling or liquefying unit. In each embodiment, the quench fluid introduction means is located downstream of the reaction zone, and is preferably located at the outlet of the oxidation reactor.

DETAILED DESCRIPTION OF THE INVENTION

Figure 1:
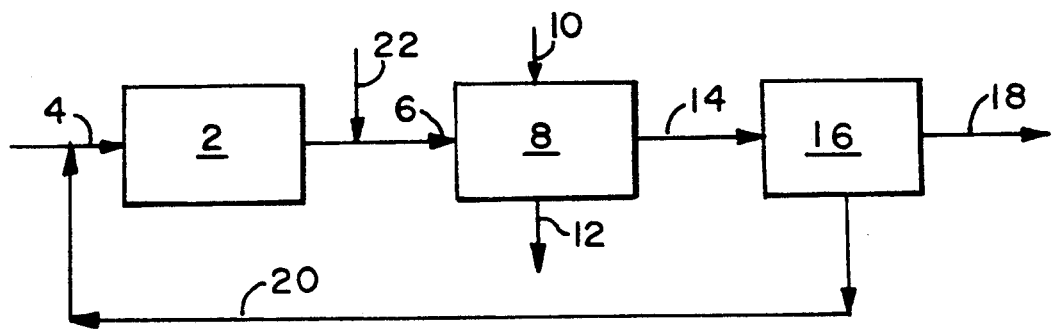
FIG. 1 illustrates, in a block diagram, one embodiment of a system for producing a petrochemical product in accordance with the present invention.

The process of the invention can be used for the manufacture of any petrochemical that is produced by the gas phase reaction at elevated temperatures of a hydrocarbon with oxygen. Typical petrochemical manufacturing processes in which the invention can be employed are:

The manufacture of cyclic anhydrides by the reaction of aromatic compounds or straight-chained $C_4$ hydrocarbons with oxygen in the presence of a vanadia-based catalyst. Examples include the production of maleic anhydride by the reaction of benzene or a saturated or unsaturated $C_4$ hydrocarbon with oxygen and the manufacture of phthalic anhydride by the reaction of o-xylene or naphthalene with oxygen.

The manufacture of an olefinically unsaturated nitriles by the reaction of lower alkanes or alkenes with oxygen and ammonia in the presence of a bismuth molybdenum oxide catalyst or an iron antimony oxide catalyst mounted on a silica or alumina support. Examples of this type of process include the reaction of propane or propylene with oxygen to produce acrylonitrile and the reaction of i-butane or i-butylene with oxygen to produce methacrylonitrile.

The manufacture of alkylene oxides by the reaction of lower alkanes or alkenes with oxygen and ammonia in the presence of a silver oxide catalyst mounted on a silica or alumina support. Examples include the reaction of ethane or ethylene with oxygen to produce ethylene oxide and the reaction of propane or propylene with oxygen to produce propylene oxide.

The manufacture of chlorinated hydrocarbons by the reaction of lower alkanes or alkenes with oxygen in the presence of a copper chloride catalyst supported on silica or alumina. Examples include the reaction of ethylene or ethane with hydrogen chloride to produce vinyl chloride or ethylene dichloride.

As is apparent from the above examples, the process of the invention can be used for the manufacture of various petrochemicals by the reaction of hydrocarbons with oxygen. However, for the purpose of simplfying the description, the invention will be described in detail as it applies to the manufacture of cyclic anhydrides by the reaction of hydrocarbons with oxygen.

The particular hydrocarbon used in the feed will, of course, depend upon which petrochemical is to be produced. In the case of cyclic anhydrides the hydrocarbon reactant is usually an aromatic or straight-chain hydrocarbon. For example, if it is desired to produce phthalic anhydride, the hydrocarbon feed is preferably o-xylene or naphthalene, and if maleic anhydride is desired, the hydrocarbon feed generally comprises benzene or straight-chain hydrocarbons containing four carbon atoms ($C_4$ hydrocarbons). n-Butane is the most preferred hydrocarbon for maleic anhydride manufacture because it is less expensive than the unsaturated $C_4$ hydrocarbons.

The oxygen source used in the process may be pure oxygen or oxygen-containing gases, such as oxygen-enriched air or other oxygen-inert gas mixtures. By oxygen-enriched air is meant air that contains more oxygen than is naturally present in air. Oxygen-inert gas mixtures include oxygen-nitrogen mixtures, oxygen-argon mixtures, oxygen-carbon dioxide mixtures, etc. Pure oxygen is preferred since its use avoids the introduction of excess inert gases, such as nitrogen and argon, into the system and the subsequent need to remove excess quantities of these inert gases from the product gas stream to prevent their buildup in the system.

The inert gas used as the quench fluid can be any inert gas, i.e. any gas that will not interfere with the production of the desired product or which is not flammable under the conditions existing in the reaction system of the invention. Typical of the inert gases that are suitable for use as quench fluids in the process of the invention are carbon dioxide, nitrogen, argon, etc. From a practical standpoint the preferred inert gases are carbon dioxide and nitrogen, since these are inexpensive and readily available. Carbon dioxide is particularly desirable because it has a relatively high heat capacity and, since it is produced as a by-product of the process of the invention, it is available in abundant supply in the waste gas stream, from which it can be easily separated. Mixtures of inert gases can be used as the quench fluid, if desired.

The inert gas quench fluid can be in the form of a gas or a liquefied gas and it may be cooled to any desired temperature. It is often preferred to use a liquefied gas as the quench fluid because of its greater cooling effect.

The invention can be better understood from the accompanying drawings, in which the same reference numerals are used to designate the same or similar pieces of equipment in different figures. Auxiliary equipment, including compressors, heat exchangers and valves not necessary for an understanding of the invention, have been omitted from the drawings to simplify discussion of the invention.

Considering first FIG. 1, the apparatus of this embodiment includes a hydrocarbon oxidation reactor 2 having a feed inlet means 4 and a product outlet line 6. Product outlet line 6 is connected to a petrochemical recovery unit 8. Unit 8 receives a solvent for the petrochemical product through inlet line 10 and discharges a liquid product solution through outlet line 12. Line 14 conducts scrubbed gas from scrubber 8 to separator 16. Separator 16 is provided with a waste gas discharge line 18, and it is also connected via recycle line 20 to feed inlet means 4. Line 22 is connected to product outlet line 6 and provides for the introduction of the inert gas quench fluid into line 6.

Reactor 2 may be any suitable reactor but it is usually of the fixed, moving, fluidized, or transport catalyst bed design. Reactor 2 may be equipped with heat exchange means (not shown) to remove heat developed in the reaction, which is exothermic. The specific design details of suitable reactors are well known and they form no part of the present invention.

Petrochemical recovery unit 8 may be a conventional gas scrubber, i.e. an absorber, usually of the packed bed design, or it may be a condenser or other appropriate product recovery unit. It is here illustrated as equipped with means for spraying water or an aqueous or nonaqueous liquid on the product gas entering this unit from reactor 2.

Separator 16 serves to remove carbon dioxide, carbon monoxide, if this component is present in the gas stream entering separator 16, and other inert gases from the scrubber effluent, and this unit can be any device which will accomplish this result. Separator 16 is usually an adsorber, an absorber or a membrane separation unit. In preferred embodiments of the invention, separator 16 is a pressure swing adsorption (PSA) unit or a temperature swing adsorption (TSA) plant.

Figure 2:
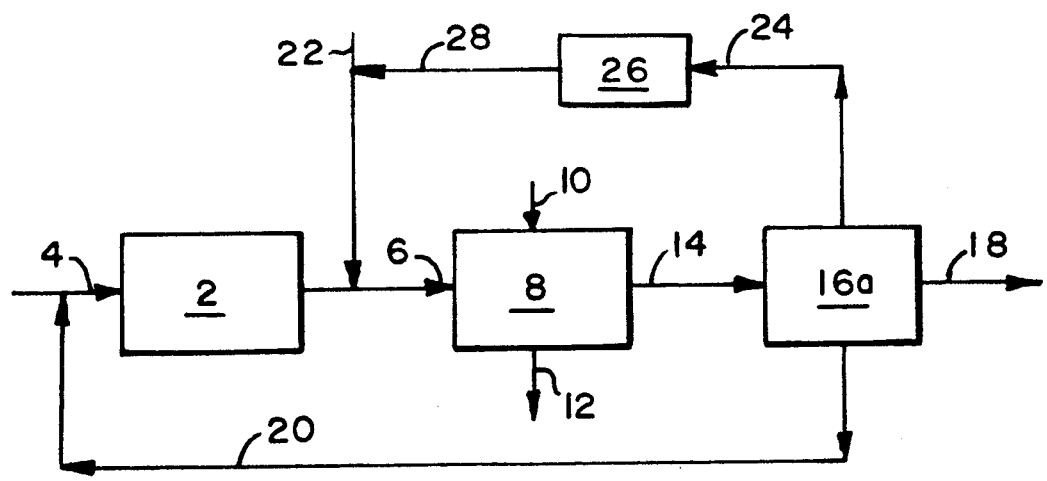
FIG. 2 illustrates, in a block diagram, an alternate embodiment of the system illustrated in FIG. 1.

FIG. 2 illustrates a variation of the system of FIG. 1. In the system of FIG. 2, the inert gas used as a quench fluid is recovered from the scrubbed gas stream and, after being cooled and perhaps liquefied, it is reintroduced into product gas line 6 as quench fluid. As shown in FIG. 2, scrubbed gas line 14 communicates with separator 16a. Similarly to the system of FIG. 1, separator 16a communicates with feed line 4 via line 20 and with a waste gas vent via line 18. The system of FIG. 2 differs from the FIG. 1 system in that the former contains a second recycle stream which leaves separator 16a through line 24 and connects to cooling or liquefication unit 26. Line 26 communicates with line 22 through discharge line 28.

Separator 16a may be comprised of a single separation means that is capable of separating a multicomponent gas stream into three streams, such as a PSA unit that produces an unadsorbed product stream and two adsorbed streams which are separately desorbed. Alternatively, separator 16a may comprise two or more individual separation units, each of which is capable of separating a gas mixture into two or more components. Unit 26 may be any suitable device that is capable of simply cooling the inert gas to the desired temperature or cooling and condensing the inert gas. For example, unit 26 may comprise a heat exchanger or a compressor and chilling device suitable for liquefying the inert gas and cooling the liquefied gas to the desired temperature.

Although not illustrated in the drawings, the systems of FIGS. 1 and 2 may include a carbon monoxide oxidation unit to convert the carbon monoxide generated in reactor 2 to carbon dioxide. This unit can be conveniently located between scrubber 8 and separator 16, in the system of FIG. 1, and between scrubber 8 and separator 16a, in the system of FIG. 2. The advantage of including a carbon monoxide oxidation step into the process of the invention is that it eliminates carbon monoxide from the gas stream entering separator 16 or 16a, thereby simplifying the gas separation process.

The specific details of the equipment units shown or described in this disclosure, including separators 16 and 16a and cooling or condensing unit 26, are well known and form no part of this invention.

In the process of the invention as practiced in the FIG. 1 system, feed, comprising a suitable hydrocarbon, an 2 through inlet means 4, which may comprise a single inlet line through which a mixture of the gaseous reactants and diluents, if any are present, are introduced into reactor 2, or it may comprise several individual inlet lines for separately introducing the reactants into the reactor. The particular inlet arrangement will generally depend upon the type of reactor used for practicing the invention. In fixed bed reactor systems the components of the feed are generally mixed before they enter the reactor and are thus fed into the reactor through a single line, whereas in fluidized bed reactor systems, the components are usually separately fed into the reactor.

The feed gases entering reactor 2 contact the catalyst and react to form the product gases. Any of the well known catalysts for oxidizing hydrocarbons to the desired petrochemical product under the specified conditions can be used in the process of the invention. In the case of cyclic anhydride production, suitable catalysts include vanadia-based catalysts, such as vanadium oxides, vanadium/molybdenum oxides, vanadium/phosphorus oxides and vanadium/titanium oxides. These catalysts and their use are conventional and well known to those skilled in the manufacture of anhydrides. The specific hydrocarbon oxidation catalysts used in the process of the invention do not form a critical part of the invention.

The conditions of the hydrocarbon oxidation are well known and form no part of the invention. Typically, the oxidation reaction is conducted at a temperature of from about 200° to 600° C., and usually from about 250° to 500° C., and at pressures typically in the range of from about 2 to 500 psig, and usually from about 3 to 300 psig. The reactants are generally passed through the reactor at a velocity in the range of from about 0.5 to 5.0 ft/sec. The ratio of oxygen to hydrocarbon in the feed is suitably in the range of 0.3:1 to 10:1 by volume.

The product gas stream leaving reactor 2 contains the desired petrochemical as the main product, and carbon dioxide and carbon monoxide as by-products. As noted above, the product stream generally also contains unreacted hydrocarbon and oxygen, and may contain small amounts of other by-products, impurity gases and non-reactive hydrocarbons. The hot product gas stream leaves reactor 2 via line 6 and rapidly comes into contact with the quench fluid entering line 6 from line 22. As indicated above, the inert gas is preferably in the liquefied state since significantly greater amounts of heat can be removed from the product gas per mole of inert gas using liquefied gas than when using a cooled inert gas because of the latent heat of evaporation required to vaporize the inert gas, and accordingly, small molar quantities of liquefied gas can provide as much cooling as considerable larger molar quantities of cooled gas. In any event, the product gas is quickly cooled to a temperature below its self-ignition point as a result of such contact. The product gas can be further cooled, if desired, by passage through an indirect heat exchanger (not shown).

After being cooled to a temperature in the range of about 30° to about 200° C., the product gas stream enters product recovery unit 8, in which the petrochemical product is removed from the gas stream. In recovery unit 8 the product gases are intimately contacted with a solvent. The solvent dissolves substantially all of the desired petrochemical in the product gas stream and the petrochemical-containing solution exits product recovery unit 8 via line 12. It is usually further treated to recover the petrochemical product. The scrubbed gas stream leaves recovery unit 8 through line 14 and enters separator 16.

As indicated above, separator 16 is preferably a PSA or TSA plant. Typically, a PSA plant may comprise two or more beds operated in a cyclic process comprising adsorption under relatively high pressure and desorption or bed regeneration under relatively low pressure or vacuum. Similarly, a TSA plant may comprise two or more beds operated in a cyclic process comprising adsorption at a relatively low temperature and desorption or bed regeneration at a relatively high temperature. The desired component or components may be obtained during either of these stages. The cycle may contain other steps in addition to the fundamental steps of adsorption and regeneration, and it is commonplace to have two or more adsorbent beds cycled 180° out of phase to assure a pseudo continuous flow of desired product. While it is conventional for the adsorption step of a PSA cycle to be carried out under pressure, it can run at ambient pressure with desorption under vacuum.

In the system illustrated in FIG. 1, a principal function of separator 16 is to separate unreacted hydrocarbon from the product gas stream for recycle to the reactor, so that the process can be optimized. Separator 16 also serves to remove excess carbon dioxide, carbon monoxide and inert gases (if present) from the stream being recycled to the reactor to prevent the build-up of these components in the system. If excess carbon dioxide and other waste gases are not removed, their concentrations in the system will increase and eventually dilute the reactants to the point at which an efficient reaction cannot take place. To avoid this problem, it is only necessary to remove amounts of carbon dioxide and the other waste gases equal to the amounts produced in reactor 2 and/or added to the system.

In the process of the invention as practiced in the system of FIG. 2, the gaseous effluent from product recovery unit 8 is treated in hydrocarbon separator 16a. Separator 16a differs from separator 16 of FIG. 1 only in that it separates the product-depleted gas into three streams. A first stream leaves separator 16a through line 20 and it contains substantially all of the unreacted hydrocarbon entering separator 16a. A second stream, comprised substantially of recovered inert gas, leaves separator 16a through line 24. Line 24 joins separator 16a to a gas cooling or gas liquefication unit 26. Unit 26 discharges cooled or liquefied gas to line 28, which is connected to line 22 through which it is reintroduced as a quench fluid into the hot gaseous product stream exiting reactor 2. A third stream leaving separator 16a contains all of the gases that are not discharged through lines 20 and 24. This stream, which is comprised substantially of waste gases, leaves separator 16a through line 18 and is either vented to the atmosphere or burned.

It will be appreciated that it is within the scope of the Present invention to utilize conventional equipment to monitor and automatically regulate the flow of gases within the system so that it can be fully automated to run continuously in an efficient manner.

ous flow rates and projected results are tabulated in TABLE II.

TABLE II

| Component | Fresh Feed | | Reactor Feed(1) | | Reactor Effluent | | PSA Feed | | Recycle | | Waste | |
|---|---|---|---|---|---|---|---|---|---|---|---|---|
| | Moles | Vol % | Moles | Vol % | Moles | Vol % | Moles | Vol % | Moles | Vol % | Moles | Vol % |
| n-Butane | 148.8 | 18.7 | 244.7 | 16.7 | 97.9 | 6.0 | 97.9 | 8.6 | 95.9 | 14.4 | 2.0 | 0.4 |
| i-Butane | 7.8 | 1.0 | 12.9 | 0.9 | 5.2 | 0.3 | 5.2 | 0.4 | 5.1 | 0.7 | 0.1 | 0.0 |
| $O_2$ | 639.3 | 80.3 | 653.0 | 44.7 | 39.2 | 2.4 | 39.2 | 3.4 | 13.7 | 2.1 | 25.5 | 5.4 |
| $N_2$ | 0.0 | 0.0 | 130.3 | 8.9 | 130.3 | 8.0 | 372.2 | 32.6 | 130.3 | 19.6 | 241.9 | 51.0 |
| Maleic Anhydride | 0.0 | 0.0 | 0.0 | 0.0 | 100.0 | 6.1 | 0.0 | 0.0 | 0.0 | 0.0 | 0.0 | 0.0 |
| CO | 0.0 | 0.0 | 57.3 | 3.9 | 163.7 | 10.0 | 163.7 | 14.4 | 57.3 | 8.6 | 106.4 | 22.4 |
| $CO_2$ | 0.0 | 0.0 | 354.7 | 24.3 | 443.4 | 27.2 | 443.4 | 38.9 | 354.7 | 53.2 | 88.7 | 18.7 |
| $H_2O$ | 0.0 | 0.0 | 9.2 | 0.6 | 653.1 | 40.0 | 19.4 | 1.7 | 9.2 | 1.4 | 10.2 | 2.1 |
| TOTAL | 795.9 | 100.0 | 1462.1 | 100.0 | 1632.7 | 100.0 | 1141.0 | 100.0 | 666.2 | 100.0 | 474.8 | 100.0 |

(1)Fresh Feed plus Recycle
Moles $N_2$ added = 241.9

The process of this invention is advantageous in its simplicity, ease of operation, low capital and operating costs and substantially reduced flammability potential. The process can be run at a relatively low per pass conversion of the feed hydrocarbon to the desired product to achieve substantially improved selectivity. It will be appreciated that a system that achieves enhanced selectivity, and hence increased overall yield of a desired product, is highly advantageous.

The invention is further illustrated by the following examples in which parts, percentages and ratios are on a volume basis.

EXAMPLE I

A vapor phase maleic anhydride production run was simulated in a fluidized bed reactor based on the use of a reactor system similar to the system of FIG. 1. The simulated feed to the hydrocarbon reactor is comprised of the Fresh Feed component and the Recycle Stream component. The reaction is simulated based on the use of a vapor phase hydrocarbon reactor containing a fluidized catalyst bed of vanadium phosphorous oxide and a pressure swing adsorber containing a molecular sieve adsorption bed. During the course of the simulated run, it is determined that 108.4 moles of liquefied carbon dioxide should be added to the effluent from the reactor to achieve the desired result. The various flow rates and projected results are tabulated in TABLE I.

Although the invention has been described with particular reference to specific experiments, these experiments are merely exemplary of the invention, and variations are contemplated. For example, the reaction can be carried out under conditions that will effect the production of other petrochemicals, as noted above. Other catalysts and adsorbents and other means of gas separation can also be used in the invention, if desired. It is emphasized that the particular oxidation reaction being carried out in the process of the invention is not critical to the invention. What is important is that the reaction is one in which a flammable or explosive oxygen-containing mixture leaves the reactor at a temperature which, in the absence of the invention, would constitute an extremely hazardous condition. The use of the invention greatly reduces the danger of a fire or an explosion.

It is also understood that the invention is not limited to the equipment arrangement illustrated in the drawings. As noted above, a carbon monoxide converter may be incorporated into the equipment train and it may be positioned between the scrubber 8 and separator 16 (or separator 16a) or it may be positioned upstream of the anhydride recovery unit 8, if desired. In fact, it may even be incorporated into reactor 2, either combined with the hydrocarbon oxidation catalyst in the form of a unitary mixed catalyst bed, or alone as a separate bed. If it is incorporated into reactor 2 as a separate bed, it is preferably located downstream of the hydrocarbon oxidation catalyst bed. It can be appreciated that

TABLE I

| Component | Fresh Feed | | Reactor Feed(1) | | Reactor Effluent | | PSA Feed | | Recycle | | Waste | |
|---|---|---|---|---|---|---|---|---|---|---|---|---|
| | Moles | Vol % | Moles | Vol % | Moles | Vol % | Moles | Vol % | Moles | Vol % | Moles | Vol % |
| n-Butane | 168.8 | 21.1 | 244.7 | 16.7 | 97.9 | 6.0 | 97.9 | 9.7 | 76.0 | 11.5 | 21.9 | 6.4 |
| i-Butane | 8.9 | 1.1 | 12.9 | 0.9 | 5.2 | 0.3 | 5.2 | 0.5 | 4.0 | 0.6 | 1.2 | 0.3 |
| $O_2$ | 622.7 | 77.8 | 653.1 | 44.7 | 39.2 | 2.4 | 39.2 | 3.9 | 30.4 | 4.6 | 8.8 | 2.6 |
| $N_2$ | 0.0 | 0.0 | 0.0 | 0.0 | 0.0 | 0.0 | 0.0 | 0.0 | 0.0 | 0.0 | 0.0 | 0.0 |
| Maleic Anhydride | 0.0 | 0.0 | 0.0 | 0.0 | 100.0 | 6.1 | 0.0 | 0.0 | 0.0 | 0.0 | 0.0 | 0.0 |
| CO | 0.0 | 0.0 | 370.6 | 25.3 | 477.0 | 29.2 | 477.0 | 47.5 | 370.1 | 55.9 | 106.8 | 31.1 |
| $CO_2$ | 0.0 | 0.0 | 171.8 | 11.8 | 260.5 | 16.0 | 368.9 | 36.7 | 171.8 | 26.0 | 197.1 | 57.3 |
| $H_2O$ | 0.0 | 0.0 | 9.1 | 0.6 | 653.0 | 40.0 | 17.1 | 1.7 | 9.1 | 1.4 | 8.0 | 2.3 |
| TOTAL | 800.4 | 100.0 | 1462.2 | 100.0 | 1632.8 | 100.0 | 1005.3 | 100.0 | 661.4 | 100.0 | 343.8 | 100.0 |

(1)Fresh Feed plus Recycle

EXAMPLE II

The simulated run of EXAMPLE I is repeated except that liquefied nitrogen is substituted for the liquefied carbon dioxide as the quench fluid. It is determined that 241.9 moles of liquefied nitrogen should be added to the reactor effluent to achieve the desired result. The varithe arrangement of the connecting fluid transfer lines for this version of the invention will be different from the arrangement illustrated in the drawings.

The scope of the invention is limited only by the breadth of the appended claims.

We claim:

1. A process for the production of a hydrocarbon partial oxidation product comprising:
    (a) contacting in the vapor phase in a reaction zone a hydrocarbon selected from the group consisting of aromatic hydrocarbons having 6 to 10 carbon atoms, alkanes having 2 to 4 carbon atoms, alkenes having 2 to 4 carbon atoms and mixtures of these, and an oxygen-containing gas in the presence of an oxidation catalyst under conditions which produce a gaseous product containing said hydrocarbon partial oxidation product;
    (b) quenching said gaseous product with an inert gas quench fluid;
    (c) recovering said hydrocarbon partial oxidation product from said gaseous product;
    (d) separating unreacted hydrocarbon from the gaseous product; and
    (e) recycling the separated unreacted hydrocarbon to said reaction zone.

2. The process of claim 1, wherein said quench fluid is selected from carbon dioxide and nitrogen.

3. The process of claim 2, wherein said quench fluid is liquefied gas.

4. The process of claim 2, wherein said quench fluid is carbon dioxide.

5. The process of claim 2, wherein said gaseous product is quenched with recycled quench fluid that is separated from said gaseous product.

6. The process of claim 1 or claim 2, wherein said petrochemical is selected from the group consisting of cyclic anhydrides, α, β-olefinically unsaturated nitriles, alkylene oxides containing 2 to 4 carbon atoms, chlorinated hydrocarbons and mixtures of these.

7. The process of claim 1 or claim 2, wherein said oxygen-containing gas is substantially pure oxygen.

8. The process of claim 1 or claim 2, wherein said reaction zone is a reactor selected from the group consisting of fixed bed reactors, fluidized bed reactors, moving bed reactors and transport bed reactors.

9. The process of claim 1 or claim 2, wherein the unreacted hydrocarbon is separated from said gaseous product by adsorption, absorption or membrane separation.

10. The process of claim 5, wherein said quench fluid is separated from said gaseous product by pressure swing adsorption.

11. The process of claim 10, wherein the unit in which said pressure swing adsorption is carried out contains an adsorbent selected from silica gel, molecular sieves and mixtures of these.

12. A process for the production of at least one cyclic anhydride selected from maleic anhydride, phthalic anhydride and mixtures of these comprising:
    (a) contacting in the vapor phase in a reaction zone a hydrocarbon selected from benzene, naphthalene, orthoxylene, four carbon straight-chain hydrocarbons and mixtures of these and oxygen in the presence of an oxidation catalyst under conditions which produce a gaseous product containing said cyclic anhydride;
    (b) quenching said gaseous product with a quench fluid selected from carbon dioxide and nitrogen;
    (c) recovering cyclic anhydride from the quenched gaseous product;
    (d) separating unreacted hydrocarbon from the cyclic anhydride-depleted gaseous product; and
    (e) recycling the separated unreacted hydrocarbon to said reaction zone.

13. The process of claim 12, wherein said cyclic anhydride is maleic anhydride and said hydrocarbon is a straight-chain hydrocarbon containing four carbon atoms.

14. The process of claim 13, wherein said hydrocarbon is n-butane.

15. The process of claim 12, wherein said cyclic anhydride is phthalic anhydride and said hydrocarbon is a orthoxylene.

16. The process of claim 12, wherein at least part of said quench fluid is obtained by recycling quench fluid that is separated from said anhydride-depleted gaseous product.

17. The process of claim 16, wherein one or both of the unreacted hydrocarbon and quench fluid are separated from said anhydride-depleted gaseous product by adsorption, absorption or membrane separation.

18. The process of claim 17, wherein one or both of the unreacted hydrocarbon and quench fluid are separated from said anhydride-depleted gaseous product by pressure swing adsorption.

19. The process of claim 18, wherein said quench fluid is carbon dioxide.

20. A process for the production of an α, β-olefinically unsaturated nitrile having 3 to 4 carbon atoms comprising:
    (a) contacting in the vapor phase in a reaction zone a hydrocarbon selected from propylene, propane, isobutylene, isobutane and mixtures of these, ammonia and oxygen in the presence of an oxidation catalyst under conditions which produce a gaseous product containing said nitrile;
    (b) quenching said gaseous product with a quench fluid selected from carbon dioxide and nitrogen;
    (c) recovering said nitrile from the quenched gaseous product;
    (d) separating unreacted hydrocarbon from the nitrile-depleted gaseous product; and
    (e) recycling the separated unreacted hydrocarbon to said reaction zone.

21. The process of claim 20, wherein said nitrile is acrylonitrile and said hydrocarbon is selected from propane, propylene and mixtures thereof.

22. The process of claim 20, wherein said nitrile is methacrylonitrile and said hydrocarbon is selected from isobutylene, isobutane or mixtures thereof.

23. The process of claim 20, wherein at least part of said quench fluid is obtained by recycling quench fluid that is separated from said nitrile-depleted gaseous product.

24. The process of claim 23, wherein one or both of the unreacted hydrocarbon and quench fluid are separated from said nitrile-free gaseous product by adsorption, adsorption or membrane separation.

25. The process of claim 24, wherein one or both of the unreacted hydrocarbon and quench fluid are separated from said nitrile-free gaseous product by pressure swing adsorption.

26. The process of claim 25, wherein said quench fluid is carbon dioxide.

27. A process for the production of an alkylene oxide having 2 to 3 carbon atoms comprising:
    (a) contacting in the vapor phase in a reaction zone a hydrocarbon selected from ethylene, ethane, propylene, propane and mixtures thereof and oxygen in the presence of an oxidation catalyst under conditions which produce a gaseous product containing said alkylene oxide;

(b) quenching said gaseous product with a quench fluid selected from carbon dioxide and nitrogen;

(c) recovering said alkylene oxide from the quenched gaseous product;

(d) separating unreacted hydrocarbon from the alkylene oxide-depleted gaseous product; and (e) recycling the separated unreacted hydrocarbon to said reaction zone.

28. The process of claim 27, wherein said alkylene oxide is ethylene oxide and said hydrocarbon is ethylene, ethane or mixtures thereof.

29. The process of claim 28, wherein said alkylene oxide is ethylene oxide and said hydrocarbon is ethylene.

30. The process of claim 27, wherein said alkylene oxide is propylene oxide and said hydrocarbon is propylene, propane or mixtures thereof.

31. The process of claim 27, wherein at least part of said quench fluid is obtained by recycling quench fluid that is separated from said alkylene oxide-depleted gaseous product.

32. The process of claim 31, wherein one or both of the unreacted hydrocarbon and quench fluid are separated from said alkylene oxide-depleted gaseous product by adsorption, adsorption or membrane separation.

33. The process of claim 32, wherein one or both of the unreacted hydrocarbon and quench fluid are separated from said alkylene oxide-depleted gaseous product by pressure swing adsorption.

34. The process of claim 33, wherein said quench fluid is carbon dioxide

35. A process for the production of a chlorinated hydrocarbon containing two carbon atoms comprising:

(a) contacting in the vapor phase in a reaction zone a hydrocarbon selected from ethylene, ethane, propylene, propane and mixtures thereof, hydrogen chloride and oxygen in the presence of an oxidation catalyst under conditions which produce a gaseous product containing said chlorinated hydrocarbon;

(b) quenching said gaseous product with a quench fluid selected from carbon dioxide and nitrogen;

(c) recovering said chlorinated hydrocarbon from the quenched gaseous product;

(d) separating unreacted hydrocarbon from the chlorinated hydrocarbon-depleted gaseous product; and (e) recycling the separated unreacted hydrocarbon to said reaction zone.

36. The process of claim 35, wherein said chlorinated hydrocarbon is vinyl chloride or ethylene dechloride and said hydrocarbon is ethylene, ethane or mixtures thereof.

37. The process of claim 35, wherein at least part of said quench fluid is obtained by recycling quench fluid that is separated from said chlorinated hydrocarbon-depleted gaseous product.

38. The process of claim 37, wherein one or both of the unreacted hydrocarbon and quench fluid are separated from said chlorinated hydrocarbon depleted gaseous product by adsorption, adsorption or membrane separation.

39. The process of claim 38, wherein one or both of the unreacted hydrocarbon and quench fluid are separated from said chlorinated hydrocarbon-depleted gaseous product by pressure swing adsorption.

40. The process of claim 39, wherein said quench fluid is carbon dioxide.

* * * * *

UNITED STATES PATENT AND TRADEMARK OFFICE
CERTIFICATE OF CORRECTION

PATENT NO. : 5,179,215
DATED : January 12, 1993
INVENTOR(S) : Ramachandran, et al It is certified that error appears in the above-indentified patent and that said Letters Patent is hereby corrected as shown below:

Column 12, line 56, delete "adsorption" and substitute --absorption--.
Column 13, line 27, delete "adsorption" and substitute --absorption--.
Column 14, line 27, delete "adsorption" and substitute --absorption--.

Signed and Sealed this

Ninth Day of November, 1993

Attest:

BRUCE LEHMAN

Attesting Officer

Commissioner of Patents and Trademarks